(12) United States Patent
Odrich

(10) Patent No.: US 6,471,666 B1
(45) Date of Patent: Oct. 29, 2002

(54) INJECTABLE GLAUCOMA DEVICE

(76) Inventor: Steven A. Odrich, 3765 Riverdale Ave., Suite 1, Bronx, NY (US) 10463

( * ) Notice: Subject to any disclaimer, the term of this patent is extended or adjusted under 35 U.S.C. 154(b) by 0 days.

(21) Appl. No.: 09/511,979

(22) Filed: Feb. 24, 2000

(51) Int. Cl.[7] .................................................. A61M 5/00
(52) U.S. Cl. ............................................... 604/8; 606/108
(58) Field of Search ........................ 604/289, 9, 93.01, 604/8, 540, 165.03, 177; 606/107, 166, 108; 623/5.14, 6.14, 5.11, 4.1, 4; 600/398, 399, 400

(56) References Cited

U.S. PATENT DOCUMENTS

| | | | |
|---|---|---|---|
| 4,037,604 A | * 7/1977 | Newkirk | 604/8 |
| 4,554,918 A | * 11/1985 | White | 604/10 |
| 4,729,761 A | 3/1988 | White | |
| 4,936,825 A | * 6/1990 | Underleider | 606/107 |
| 5,041,081 A | * 8/1991 | Odrich | 604/9 |
| 5,071,408 A | * 12/1991 | Ahmed | 606/108 |
| 5,073,163 A | * 12/1991 | Lippman | 604/9 |
| 5,178,604 A | * 1/1993 | Baerveldt | 604/8 |
| 5,370,607 A | 12/1994 | Memmen | |
| 5,372,577 A | 12/1994 | Ungerleider | |
| 5,397,300 A | 3/1995 | Gaerveldt et al. | |
| 5,454,796 A | 10/1995 | Krupin | |
| 5,626,558 A | 5/1997 | J. Suson | |
| 5,743,868 A | 4/1998 | Brown et al. | |
| 5,752,928 A | 5/1998 | Gregoire de Roulbac et al. | |
| 5,785,674 A | * 7/1998 | Mateen | 604/9 |
| 5,830,173 A | 11/1998 | Avery et al. | |
| 5,893,837 A | 4/1999 | Eagles et al. | |
| 5,968,058 A | 10/1999 | Richter et al. | |

* cited by examiner

*Primary Examiner*—Ira S. Lazarus
*Assistant Examiner*—Tu Cam Nguyen
(74) *Attorney, Agent, or Firm*—Notaro & Michalos P.C.

(57) ABSTRACT

A glaucoma device includes an aqueous tube shunt implant with a foldable reservoir plate for injecting below the conjunctiva of a patient's eye via a hollow cannula. The device has an internal ostium with a flared lip at one end of a shaft having a flattened wing extending to the sides. A foldable plate and reservoir are provided at the at the other end of the shaft and connected to an external ostium of the shaft. The flattened wing presents a flat surface to the overlying conjunctiva and helps position the device when used. The device is preferably made of silicone or acrylic so that the entire implant is foldable and may be rolled up for insertion via the cannula. Other improvements and a method for implanting the device are disclosed as well.

16 Claims, 2 Drawing Sheets

INJECTABLE GLAUCOMA DEVICE

FIELD AND BACKGROUND OF THE INVENTION

The present invention relates generally to the field of glaucoma treatment devices and in particular to a new and useful implantable glaucoma shunt for relieving internal pressure in a patient's eye. The new glaucoma shunt has a foldable plate and reservoir which permit the shunt to be injected into a patient's eye using a cannula.

Implantable glaucoma shunts are known which require more extensive surgery or require the shunt to be sutured into place on the patient's eye. Other shunts are simply cylinders which are injected nearly perpendicularly into the patient's eye and held by frictional fit by eye tissue.

U.S. Pat. No. 5,127,901 teaches an ophthalmic implant for is draining aqueous humor from the anterior chamber of the eye having a transcleral conduit having an inlet opening at one end thereof for communicating with the anterior chamber of an eye, and an outlet opening at an opposite end of the conduit for draining fluid from the anterior chamber. An elongated arch shaped subconjunctival channel is connected to the conduit and has an inlet opening into the channel for communicating with the outlet opening of the conduit, the channel having an outlet openings for discharging fluid from the conduit, subconjunctivally over the sclera of the eye. A one-way flow resisting valve is provided in the conduit for allowing a flow of fluid to pass under resistance and in only one direction from the inlet to the outlet of the conduit, whereby pressure in the anterior chamber is relieved while avoiding excessive outflow of fluid from the anterior chamber.

The shunt of U.S. Pat. No. 5,127,901 is not foldable, however and must still be implanted into a patient's eye using surgical cutting techniques.

Other glaucoma shunts include U.S. Pat. No. 5,743,868, for example, which discloses a cylindrical drainage tube which can be injected through the surface of a patient's cornea. The tube is formed from a hollow rigid cylinder surrounding a porous core layer. The device is simply pushed into place using a plunger implant mechanism and positioned so that the exterior end is substantially flush with the surface of the cornea. The device lacks any wings or means for securing the device underneath the conjunctiva or sclera.

A plunger device for implanting cylindrical glaucoma drains is taught by U.S. Pat. No. 5,893,837. The device is placed at the end of the plunger for insertion through eye tissue. The glaucoma devices inserted using the plunger do not have wings or reservoir flaps.

U.S. Pat. No. 5,752,928 teaches a glaucoma device having a reservoir plate made of a flexible material, such as silicone rubber. The device is implanted through an incision in the eye followed by suturing the incision.

U.S. Pat. No. 5,178,604 is for a glaucoma implant having a flexible elastomeric plate. The plate is curved to conform to the curvature of a person's eye. The plate is inserted through an incision into a position beneath the portion of the eye known as Tenon's capsule and over the sclera. The plate is sutured to the sclera. The plate can be folded to permit a smaller incision in the eye. A preferred material for the plate is silicone elastomer. The Baerveldt '604 patent does not teach injecting the device into place and no provision is made for securing the device without sutures until after tissue has grown around the device.

A continuation-in-part patent, U.S. Pat. No. 5,397,300, discloses a similar device. The glaucoma device in U.S. Pat. No. 5,397,300 also has a flexible plate. The plate has at least one through hole to permit the growth of scar tissue to assist holding the plate-in position following suturing during the implant procedure.

A laser is taught for use in making the incision for implanting a glaucoma device in U.S. Pat. No. 5,626,558. The device has a plate connected to the exterior end of a tube forming the body of the device. The plate-may be sutured to the sclera to hold the device in place after insertion.

U.S. Pat. No. 5,370,607 teaches an implant device having a pair of wings extending from a reservoir around the body of a person's eye. The device is inserted through an incision and sutured into place. A tab positioned between the reservoir and the drainage tube in the center of the reservoir between the wings is used to suture the device in place. The wings are used to stabilize the placement of the device underneath the ocular muscles.

U.S. Pat. No. 4,554,918 shows a glaucoma device having a reservoir with a flat attachment plate having holes therethrough for receiving sutures or permitting tissue ingrowth. The plate is preferably made of silicone rubber, polymethyl methacrylate polymer or other similar polymers, among other compositions. A pair of flat rectangular fins extending from the sides of the tube are used to secure the device to the sclera beneath a small flap.

The prior glaucoma shunt devices are either simple tubes or ports injected directly through the eye, rather than implanted below the conjunctiva, or require tissue cutting, extensive-tissue manipulation and suturing to successfully implant the device below the conjunctiva.

SUMMARY OF THE INVENTION

It is an object of the present invention to provide a glaucoma shunt which can be implanted in a patient's eye using minimally invasive surgery techniques.

It is a further object of the invention to provide an implantable glaucoma device which does not require sutures to hold the device in position once the device has been implanted in a patient's eye.

Accordingly, a new glaucoma device is provided comprising a foldable aqueous tube shunt implant for injecting below the conjunctiva of a patient's eye via a hollow cannula. The device is used to drain aqueous humor from the anterior chamber of a person's eye to help control glaucoma and intrabcular pressure.

The device has an internal ostium with a flared lip at one end of a shaft having a flattened wing extending to the sides. A foldable plate and reservoir are provided at the other end of the shaft and connected to an external ostium of the shaft. The flattened wing presents a flat surface to the overlying conjunctiva and helps position the device when used.

The device is preferably made of silicone or acrylic so that the entire implant is foldable and may be rolled up for insertion via the cannula.

Since the entire implant device may be folded and injected into place within a person's eye, the implant can be implanted using a cannula following laser sclerostomy in a minimally invasive procedure and without incisional surgery. Sutures are not needed to hold the implant in place once it has been injected into position. The lip on the inner ostium holds the device in place.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
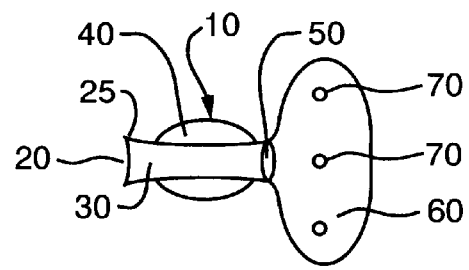
FIG. 1 is a top plan view of the glaucoma device of the invention.

Referring now to the drawings, in which like reference numerals are used to refer to the same or similar elements, FIG. 1 shows the glaucoma device 10 of the invention having internal ostium 20 with a flared lip 25 at the end of a drainage shaft 30. The flared lip 25 tapers from the internal ostium 20 to the shaft 30, so that the diameter of the internal ostium 20 is greater than that of the shaft 30.

Foldable wings 40 are formed on the sides of the drainage shaft 30. An external ostium 50 is provided at the other end of the shaft 30 on the upper side of the shaft. A foldable plate 60 is attached to the end of shaft 30 opposite the internal ostium 20. The plate 60 has openings 70 in the top surface.

Figure 2:
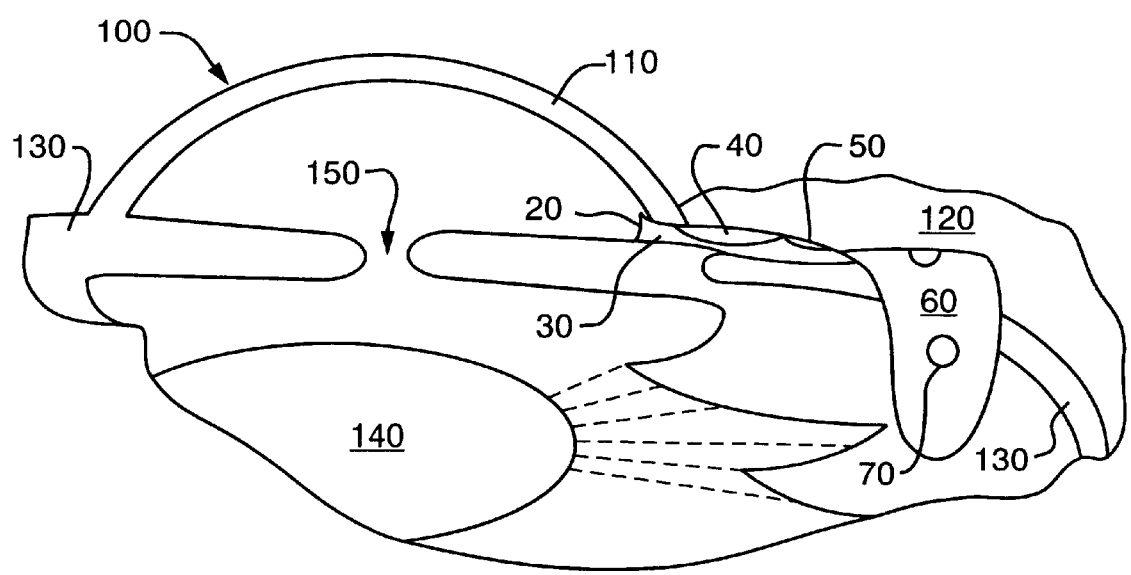
FIG. 2 is a partial sectional side elevational view of the glaucoma device implanted into a patient's eye.

FIG. 2 shows the glaucoma device 10 implanted in a patient's eye 100. The device 10 is positioned underneath the conjunctiva 120 and rests on the patient's sclera 130. The internal ostium 20 is inserted through the inner edge of the cornea 110 adjacent the pupil 150 and sclera 130. The lens 140 of the patient's eye 100 is shown for reference.

As seen in the drawing, the glaucoma device 10 is positioned with the internal ostium 20 extending inside the eyeball, while the external ostium 50 and plate 60 are outside the eyeball. Higher pressure liquid inside the patient's eye 100 can naturally drain through the glaucoma shunt device 10 via the ostiums 20, 50 and shaft 30 to outside the eye. Thus, internal eye, or intraocular, pressure is relieved by the presence of the glaucoma shunt device 10 of the invention.

The foldable wings 40 help to position the device 10 by providing a flat surface for the overlying conjunctiva 120 to rest upon. The wings 40 should be oriented facing toward the conjunctiva 120 to maximize their benefit. The plate 60 acts as a foreign object inside the patient's eye which causes tissue to grow around the plate 60 over a period of time. The tissue growth assists in holding the device 10 in place over an extended period of time.

The entire glaucoma device 10 is made of a foldable biocompatible material. Suitable biocompatible materials include poly methylmethacrylate (PMMA), silicone or acrylic. The materials used to make the plate 60 may be-rolled up to a cylinder roughly having the same size diameter as the drainage shaft 30. Similarly, the wings 40 may be folded up around the sides of the drainage shaft 30.

Preferably, the diameter of the drainage shaft 30 is about 350 microns and the device 10 is about 12 mm long. The diameter of the internal ostium 20 is preferably about 500 microns. The wings 40 are between 1 and 2 mm across when unfolded.

Figure 3:
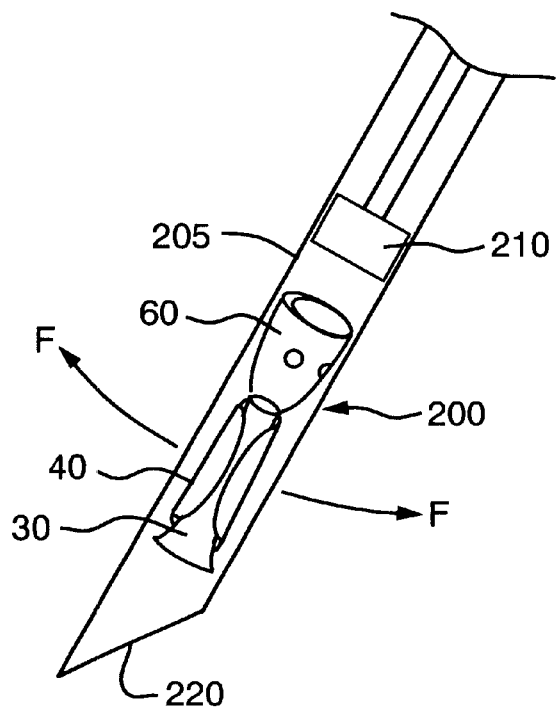
FIG. 3 is a sectional side elevational view of the glaucoma device inside an implantation cannula.

FIG. 3 displays the glaucoma device 10 rolled up inside a cannula injector 200 having a plunger 210 and insertion opening 220. The reservoir plate 60 is rolled up to fit within the cannula shaft 205. The plunger 210 can be activated using any known method for pushing objects with plungers, such as by a simple mechanical handle of a type commonly found on syringes. In a preferred embodiment of the cannula injector 200, the cannula shaft 205 can flex perpendicularly to the longitudinal axis, as shown by arrows F, but does not compress along the longitudinal axis. The flexion assists the implantation of the glaucoma device 10 in a patient's eye.

The cannula injector 200 can be used to implant the glaucoma device 10 after a laser has been used to make an opening in the patient's eye, such as by laser sclerostomy (ab externo or ab interno). Alternatively, the device 10 can be inserted through an opening in the eye created by a prior trabeculectomy.

A much smaller opening can be used to implant the glaucoma device 10 of the invention, compared to a non-folding implant, since the device 10 is inserted using cannula injector 200. The opening has only to be sufficiently large to permit the cannula opening 220 to pass through. The cannula injector 200 preferably has a diameter of between 500–700 microns and is made to permit flexibility perpendicular to the longitudinal axis, but not compression of the longitudinal axis. The device 10 is inserted and unfolded beneath the conjunctiva 120 of the patient's eye. The internal ostium 20 and flared lip 25 are positioned through the side of the eyeball. The flared lip 25 and plate 60 hold the device in place in conjunction with the wings 40, so that no suturing is needed.

Since the laser sclerostomy and implant injection can both be done in a doctor's office, the device 10 provides a new level of convenience and simplicity heretofore unknown in glaucoma treatment. When a prior trabeculectomy opening is used, the procedure is further simplified by the elimination of the need for laser. A patient no longer has to visit the hospital or endure a lengthy procedure to have a glaucoma shunt implanted. The recovery time is much shorter, since even when a laser is used, the laser creates a much smaller opening through the eye of the patient, and no suturing is needed to secure the device 10 in place in the patient's eye 100.

The device 10 permits the in-office conversion of previous failed non-implant filtration surgery to successful tube shunt mediated filtration., The glaucoma device 10 allows patients whose trabeculectomies have failed to undergo an in-office implantation using the old, failed trabeculectomy site to re-establish the flow of aqueous out of the eye. Thus, additional incisional surgery in a hospital operating room is not required when the device 10 of the invention is used.

Figure 4:
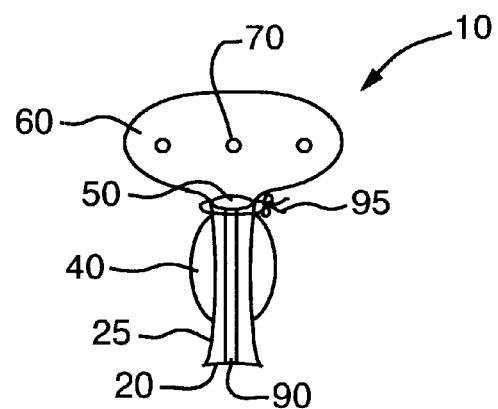
FIG. 4 is a top plan view of a further embodiment of the glaucoma device of the invention.

In a further embodiment of the glaucoma device 10 shown in FIG. 4, a pigmented stripe 90 is provided longitudinally down one side of the drainage shaft 30. The stripe 90 is colored to be distinguishable from the tissue in which the device 10 is going to be implanted as described above. Preferably, the stripe 90 is colored differently from the eye tissues surrounding where the device 10 will be implanted.

Once the device 10 has been implanted, a laser having an appropriately tuned frequency is used to make one or more fenestrations or holes through the wall of drainage shaft 30 where the stripe 90 is located. The pigment of the stripe 90 and the frequency of the laser should be selected so that the laser will pass through the tissues surrounding-the implant device 10 and cause the least amount of damage possible. The number of holes created in the striped portion 90 of the drainage shaft 30 wall will affect the flow rate of aqueous through the device 10 from the patient's eye.

In a preferred version of the device 10 having the pigmented stripe 90, the drainage shaft 30 wall thickness in the area of the stripe 90 is reduced from that of the remainder of the drainage shaft 30. The laser can more easily be used to perforate the wall of the drainage shaft 30 where the stripe 90 is provided.

In yet another embodiment of the device 10, a ligature suture 95 is provided around an end of the tube adjacent the external ostium 50. The ligature suture 95 is tied around the end in a manner which permits the ligature suture 95 to be tightened once the device 10 has been implanted. The ligature suture 95 is used to constrict the flow of aqueous through the device 10 when it is initially placed in the patient's eye. It is well known that the initial depressurization of the eye during this type of glaucoma treatment procedure results in much increased liquid flow than after a period of time has passed. By initially constricting the flow of aqueous through the device 10 using the ligature suture 95, the patient's eye is prevented from being excessively depressurized. A ligature suture 95 is used since it will dissolve after a short period of time, such as 10–20 days, and once the suture 95 is dissolved, normal fluid flow through the device 10 is allowed.

While a specific embodiment of the invention has been shown and described in detail to illustrate the application of the principles of the invention, it will be understood that the invention may be embodied otherwise without departing from such principles.

What is claimed is:

1. A glaucoma shunt implantation kit comprising:
   a glaucoma shunt having a drainage shaft, an internal ostium at one end of the drainage shaft, the internal ostium having a flared lip, an external ostium adjacent the second end of the drainage shaft on an upper side of the shaft, a foldable plate connected to the second end of the drainage shaft, a pair of foldable wings extending from each of the left and right sides of the drainage shaft; and
   a hollow cannula injector having means for pushing the glaucoma'shunt through the injector after. the glaucoma shunt has been inserted within the injector with the plate and wings folded to a diameter less than an inner diameter of the injector.

2. A kit according to claim 1, wherein the cannula injector can flex perpendicular to its longitudinal axis to facilitate implantation of the glaucoma shunt.

3. A kit according to claim 1, wherein the glaucoma shunt is made of a biocompatible material.

4. A kit according to claim 3, wherein the biocompatible material is selected from the group consisting of PMMA, acrylic and silicone.

5. A kit according to claim 1, wherein the inner diameter of the injector is between 500 and 700 microns.

6. A method of implanting a glaucoma shunt in a patient's eye, comprising:
   providing a glaucoma shunt having a drainage shaft, an internal ostium at one end of the drainage shaft, the internal ostium having a flared lip, an external ostium adjacent the second end of the drainage shaft on an upper side of the shaft, a foldable plate connected to the second end of the drainage shaft, a pair of foldable wings extending from each of the left and right sides of the drainage shaft;
   folding the glaucoma shunt to fit within a hollow cannula injector;
   providing an implant opening in the patient's eye;
   inserting the cannula injector with the glaucoma shunt through the implant opening;
   injecting the glaucoma shunt below a conjunctiva of the patient's eye;
   positioning the glaucoma shunt with the internal ostium inside the patient's eye and the wings and plate unfolded;
   removing the cannula injector; and
   closing the implant opening.

7. A method according to claim 6, wherein providing the implant opening comprises performing a laser sclerostomy on a patient's eye to create the implant opening.

8. A method according to claim 7, wherein the glaucoma shunt further comprises a longitudinal pigmented stripe on the drainage shaft, the method further comprising using a laser, after injecting and positioning the glaucoma shunt, to make fenestrations in the drainage shaft where the pigmented stripe is located.

9. A method according to claim 7, further comprising tightening a ligature suture around the drainage shaft to constrict the initial flow of aqueous through the glaucoma shunt.

10. A method according to claim 6, wherein providing the implant opening comprises using the site of a previous trabeculectomy as the implant opening.

11. A method according to claim 10, wherein the glaucoma shunt further comprises a longitudinal pigmented stripe on the drainage shaft, the method further comprising using a laser, after injecting and positioning the glaucoma shunt, to make fenestrations in the drainage shaft where the pigmented stripe is located.

12. A method according to claim 7, further comprising tightening a ligature suture around the drainage shaft to constrict the initial flow of aqueous through the glaucoma shunt.

13. A glaucoma device for implanting in the eye of a patient to relieve intraocular pressure, the device comprising:
   a drainage shaft;
   a longitudinal pigmented stripe on the drainage shaft;
   an internal ostium at one end of the drainage shaft, the internal ostium having a flared lip;
   an external ostium adjacent the second end of the drainage shaft on an upper side of the shaft;
   a foldable plate connected to the second end of the drainage shaft; and
   a pair of foldable wings extending from each of the left and right sides of the drainage shaft.

14. A glaucoma device according to claim 13, wherein the pigmented stripe is colored differently from tissues found in a human eye.

15. A glaucoma device according to claim 13, wherein the drainage shaft wall has a reduced thickness where the pigmented stripe is located relative to the remainder of the drainage shaft wall.

16. A glaucoma device for implanting in the eye of a patient to relieve intraocular pressure, the device comprising:
   a drainage shaft;
   an internal ostium at one end of the drainage shaft, the internal ostium having a flared lip;
   an external ostium adjacent the second end of the drainage shaft on an upper side of the shaft;
   a foldable plate connected to the second end of the drainage shaft; and
   a pair of foldable wings extending from each of the left and right sides of the drainage shaft, wherein the plate and wings are made of a biocompatible material and rolled to have a diameter, which is about the same as a shaft diameter of the drainage shaft.

* * * * *